United States Patent
van den Berg

(12) 
(10) Patent No.: US 6,216,696 B1
(45) Date of Patent: Apr. 17, 2001

(54) ARTIFICIAL RESPIRATION DEVICE

(75) Inventor: Paulus Cornelis Maria van den Berg, Amsterdam (NL)

(73) Assignee: Ideamed N.V., Willemstad (AN)

( * ) Notice: Subject to any disclaimer, the term of this patent is extended or adjusted under 35 U.S.C. 154(b) by 0 days.

(21) Appl. No.: 09/319,436
(22) PCT Filed: Dec. 5, 1997
(86) PCT No.: PCT/NL97/00669
  § 371 Date: Jul. 7, 1999
  § 102(e) Date: Jul. 7, 1999
(87) PCT Pub. No.: WO98/24498
  PCT Pub. Date: Jun. 11, 1998

(30) Foreign Application Priority Data

Dec. 6, 1996 (NL) .................................................. 1004721

(51) Int. Cl.$^7$ ................................................ A61M 16/00
(52) U.S. Cl. ................................ 128/207.14; 128/200.24
(58) Field of Search .................... 128/207.14, 200.24; 606/191, 198, 127, 153, 114; 600/201, 206

(56) References Cited

U.S. PATENT DOCUMENTS

| 2,541,691 | 3/1951 | Eicher . | |
|---|---|---|---|
| 3,996,938 | 12/1976 | Clark, III . | |
| 4,650,466 | 3/1987 | Luther . | |
| 4,921,484 | * 5/1990 | Hillstead | 604/104 |
| 5,065,757 | 11/1991 | Dragisic et al. . | |
| 5,163,912 | * 11/1992 | Gay et al. | 604/164 |
| 5,304,121 | 4/1994 | Sahatjian . | |

FOREIGN PATENT DOCUMENTS 6 615 648    5/1968   (NL) .

* cited by examiner

*Primary Examiner*—Dennis Ruhl
*Assistant Examiner*—Mital Patel
(74) *Attorney, Agent, or Firm*—Young & Thompson

(57) ABSTRACT

An artificial respiration device for giving artificial respiration to a human being or mammal, includes a tube designed to pass through the mouth and the pharynx towards the entrance of the trachea until beyond the vocal chords. The far end of the tube for passing towards the trachea opens out into a flexible hose having a greater diameter than the tube, the hose is made of a material or materials with a certain memory. A pulling force exerted on the end of the hose makes the hose constrict, in such a way, that after the hose has been constricted, memory action causes it to assume substantially its original shape after the removal of the pulling force.

5 Claims, 2 Drawing Sheets

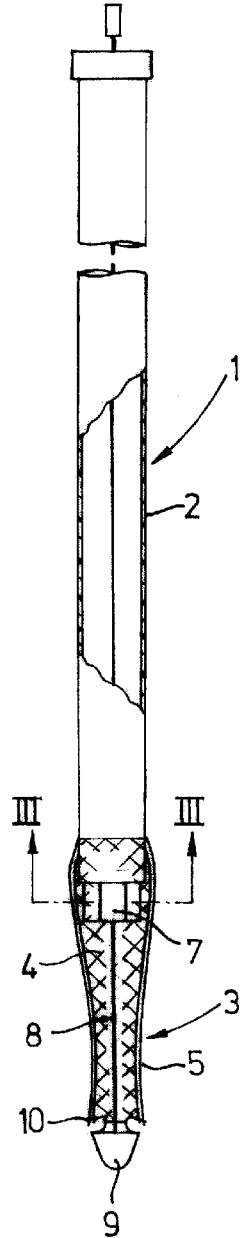
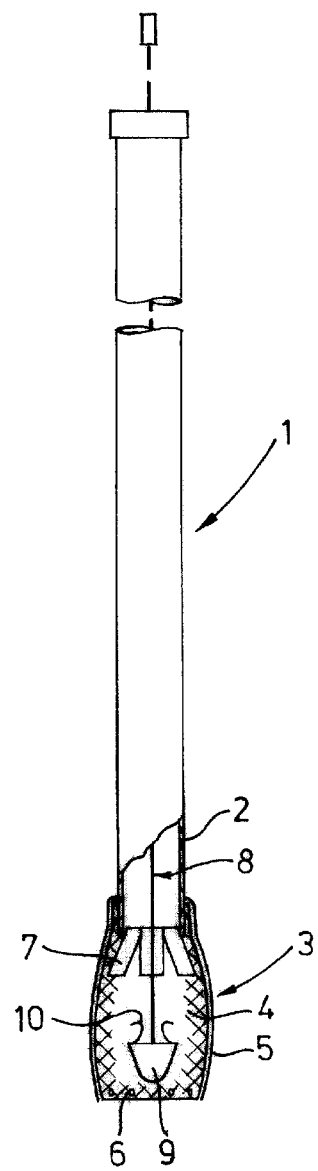
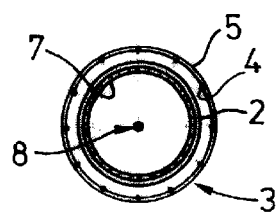

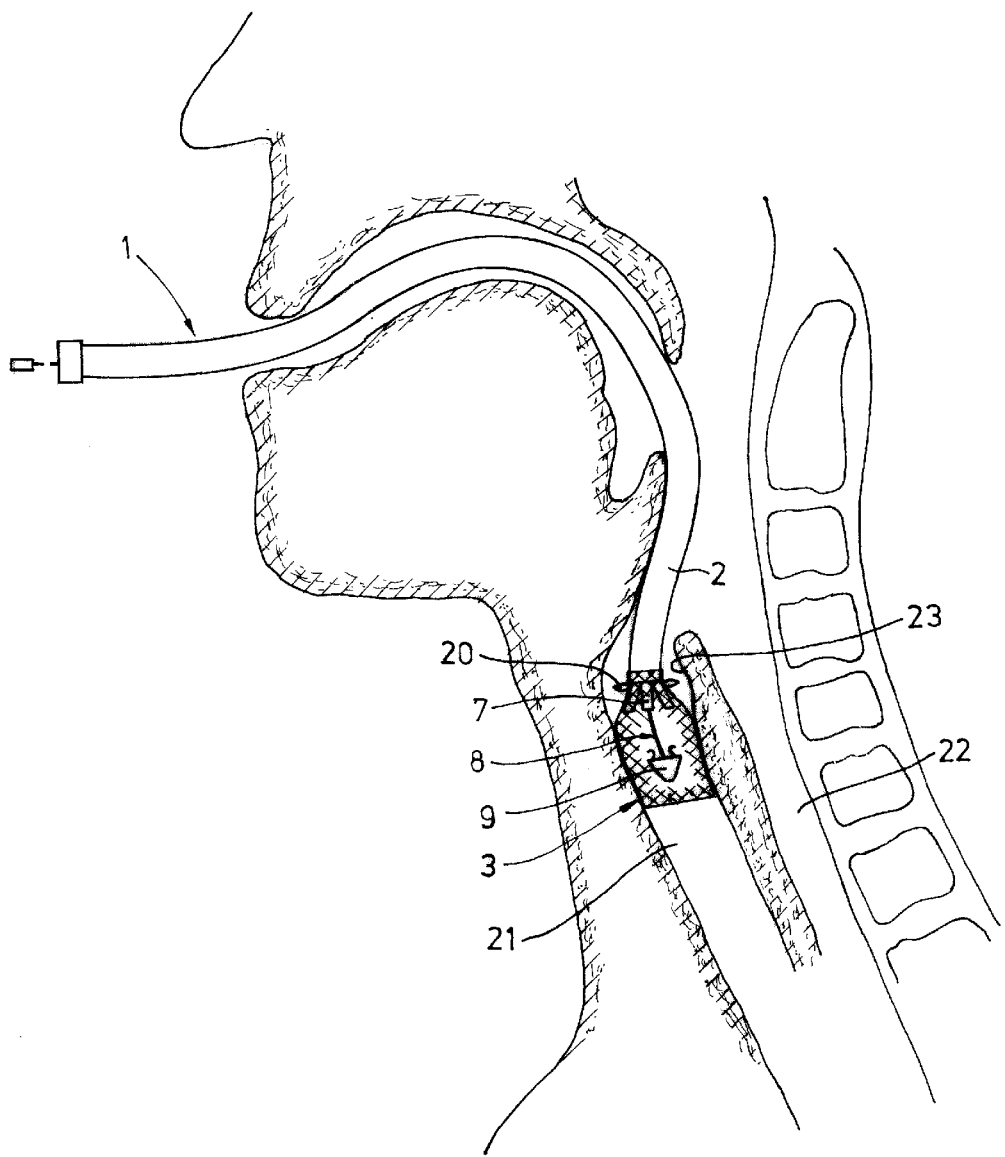

ARTIFICIAL RESPIRATION DEVICE

The invention relates to an artificial respiration device for giving artificial respiration to a human being or mammal, comprising a tube, having a proximal end and a distal end, the distal end to be passed through the mouth and the pharynx towards the end of the trachea.

Artificial respiration devices designed for passing beyond the vocal chords are generally known in medical practice. They are used in numerous operations and in intensive care, in order to guarantee a good air passage between the lips and the windpipe, or trachea. At the same time, the artificial respiration devices ensure that no moisture, for example from the gullet, can pass into the trachea. An artificial respiration device generally comprises a flexible plastic tube which is inserted through the mouth and the pharynx into the trachea. In order to facilitate its insertion, the tube has a certain curvature. A balloon is fixed around the far end of the tube to be moved towards the lungs, near the end. The tube is inserted into the trachea so far that said balloon has passed the vocal chords in its entirety. After placing of the tube, the balloon is inflated by means of a hose, so that the space between the outside wall of the tube and the walls of the trachea is shut off in an airtight manner. Thereafter, air pressure can be built up by artificial respiration means in the trachea and in the lungs lower down.

Artificial respiration devices designed for passing beyond the vocal chords generally guarantee great operational reliability. These artificial respiration devices are therefore employed when a patient has to be given artificial respiration for a long time, or when the artificial respiration device itself is difficult to reach during the artificial respiration. This is the case, for example, when a patient is lying on his stomach during an operation.

The use of artificial respiration devices according to the prior art designed for passing through the mouth and the pharynx towards the entrance of the trachea until beyond the vocal chords have a major disadvantage. The balloon on the end of the tube has to be inflated at a relatively high pressure, in order to guarantee that the trachea is adequately shut off. That pressure is of the order of 20–30 cm water (approx. 2000–3000 Pa). This high pressure at which the balloon is pressed against the mucous membrane on the inside of the trachea can press the blood vessels shut, which impedes the supply of blood to the mucous membrane. As a result of this, if an endotracheal tube is used for a long period, the mucous membrane can die off, ulcers can form on the mucous membrane and subsequently holes may even appear in the wall of the trachea.

Another disadvantage of the artificial respiration devices according to the prior art designed for passing beyond the vocal chords is that these tubes can damage the vocal chords during insertion. For the tubes to work, the far end of the tube with the balloon around it has to be inserted between the vocal chords. That means that a relatively large volume has to be forced through between the very fragile vocal chords. If the vocal chords are damaged by the tube, this can lead to infections, the formation of scar tissue, blockage of the trachea or permanent hoarseness for the patient.

The object of the present invention is to make an artificial respiration device which does not have the disadvantages of the known artificial respiration devices according to the prior art designed for passing beyond the vocal chords. The invention aims in particular to make an artificial respiration device which shuts off the trachea well and can be inserted in a simple manner, without running the risk of the tube damaging the larynx or the upper air passages.

That object is achieved by the fact that the distal end of the tube opens out in a flexible hose, wherein the proximal end of the hose is fixed to the distal end of the tube, and the distal end of the hose extending away from the tube, said hose being made of a material or materials with certain memory, and in that the device comprises an insertion element movably mounted inside the tube, said insertion element having a proximal end and a distal end, the distal end of the insertion element being fixed to the distal end of the hose, and the proximal end of the insertion element protruding from the proximal end of the tube, wherein the insertion element by means of the proximal end thereof is movable with respect to the tube from a first position wherein the distal end of the insertion element in essence exerts no pulling force on the distal end of the hose, to a second position, towards the distal end of the tube wherein the distal end of the insertion element exerts a pulling force on the distal end of the hose in order to make the hose constrict.

During the insertion of the artificial respiration device according to the present invention. the hose can be constricted by means of a pulling force. That means that the hose fixed on the distal end of the tube can pass the vocal chords with a relatively small diameter. The risk of damage to the vocal chords is consequently reduced. After the hose has passed the vocal chords with a relatively small diameter, the pulling force on the hose is removed. The memory action of the material of the hose causes the hose subsequently to assume substantially its original shape. With the outside wall, the hose then nestles against the mucous membrane on the inside wall of the trachea. The sealing of the trachea is therefore not—as in the artificial respiration devices according to the prior art—ensured by in inflatable element on which high pressure is exerted but by the hose pressing with a relatively low force against the mucous membrane on the inside wall of the trachea. A pressure of approx. 5 cm water (approx. 500 Pa) is sufficient to guarantee that the trachea is shut off. At such a low pressure the blood circulation of the mucous membrane will not be endangered. Since only the hose on the end of the tube, and not the tube itself, is passed through the vocal chords, an additional advantage of the artificial respiration device according to the present invention is that the inside diameter of the tube is selected to be just about the same as the outside diameter of artificial respiration devices according to the prior art. The resistance to the air flow through the artificial respiration device according to the present invention will be relatively low, compared with the resistance to the air flow through artificial respiration devices according to the prior art. Because of the presence of the insertion element, which insertion element can act upon the distal end of the hose, applying a longitudinal force to the hose and removing the longitudinal force from the opening of the tube can be regulated from the from the proximal end of the tube, The use of the artificial respiration device according to the present application is improved if the distal end of the insertion element is detachably fixed to the distal end of the hose. According to the invention it is possible that the distal end of the hose comprises openings, and the distal end of the insertion element comprises hooks which can project through the openings of the hose, The insertion element can engage in the openings on the hose, by means of the hooks at the distal end thereof. This has the advantage that the longitudinal force on the hose, which is necessary for constricting the hose, can be transmitted to the hose by means of the insertion element. The distal end of the hose can be fixed to the insertion element, in order to exert a pulling force thereon.

The memory action of the hose is reinforced if the distal end of the tube is provided with flaps. The flaps, which are moved towards each other with a certain resilience during the insertion, with their resilience help the hose to assume its original shape after the pulling force on the hose has been removed.

It is advantageous to construct the hose from a reticulated base, covered with a thin flexible film. The reticulated base, for example of an elastomer, provides the memory action of the tube on which the present invention is based. The thin flexible film, for example of an elastomer, then provides al airtight closure of the hose.

Every effort is made to ensure that the insertion element is made of aluminium covered with a plastic. That has the advantage that the aluminium is easily deformed by hand. By means of the insertion element which can be deformed by hand, the artificial respiration device according to the present invention can be given a certain curvature, which can facilitate the positioning of the tube.

The operation and use of the artificial respiration device according to the present invention is explained with reference to the following figures, which show an exemplary embodiment.

FIG. 1 is a sketch of the artificial respiration device according to the present invention, with the hose in the constricted position.

FIG. 2 is a sketch of the artificial respiration device according to the present invention, with the hose in the unconstricted position.

FIG. 3 is a cross-section of the artificial respiration device at the level of the flaps.

FIG. 4 is a sketch of the artificial respiration device according to the present invention introduced into a human being.

FIG. 1 shows the distal end of the artificial respiration device 1 to be moved towards the lungs. The end of the tube 2 opens out into hose 3. The end of the tube 2 is provided with a number of flaps 7. The hose 3 is composed of a reticulated material 4 with a thin film 5 thereon. At the end of the hose 3 openings 6 are made in the film 5. A pulling force can be exerted upon the hose 3 by means of an insertion element 8. The insertion element 8 ends in a spherical part 9 and is provided with a number of fixing elements 10, for example hooks. The end of the hose 3 can be hooked onto the fixing elements 10. By pushing the insertion element 8 out of the far end to be moved towards the lungs, a pulling force is exerted upon the hose 3 and constricts the hose 3. It can be seen in FIG. 1 that the diameter of the constricted hose 3 is smaller than the diameter of the tube 2. By subsequently moving the insertion element 8 in the other direction, the fixing elements 10 are detached from the hose, and the hose 3 can resume substantially its original shape as a result of memory action.

FIG. 2 is a sketch of the artificial respiration device 1 in the situation where no pulling force is exerted upon the hose 3. The diameter of the unconstricted hose 3 is now greater than that of the tube 2. The flaps 7, fixed on the end of the tube 2, are folded out, as can be seen in FIG. 2. When a pulling force is exerted on the hose 3, as shown in FIG. 1, the flaps 7 are moved towards each other and build up a certain resilience. When the pulling force on the hose 3 is removed, as shown in FIG. 2, the flaps 7 with their resilience help the hose 3 to assume its original shape. Since the flaps 7 fold out after the removal of the pulling force, the insertion element 8 with the spherical end 9 and the fixing elements 10 thereon can easily be pulled out of the hose 3 and further through the tube 2.

FIG. 3 is a cross-section of the artificial respiration device 1 at the level of the flaps 7. The figure shows the situation where the flaps 7 have been folded towards each other. The figure shows the situation where six flaps 7 together form a circular section. Of course, it is also possible to make a circular section with another number of flaps, for example four, five, or eight.

FIG. 4 is a sketch of the artificial respiration device 1 inserted into a person. The tube 2 is inserted through the mouth and the pharynx so far in the direction of the trachea 21 that the flaps 7 are situated between the vocal chords 20. The resilience stored in the flaps 7 guarantees a free air passage at the level of the vocal chords 20 at all times. The hose 3 is situated substantially in the entrance of the trachea 23 at the lung side of the vocal chords 20. FIG. 4 shows the situation where the end of the hose 3 is detached from the insertion element 8. The hose 3 has assumed substantially its original shape and thus rests against the mucous membrane 23 on the wall of the trachea 21. Although the force exerted by the hose 3 on the mucous membrane 23 of the trachea 21 (approx. 5 cm water) is relatively small, the hose 3 shuts off the trachea 21 sufficiently. Air pressure can be built up below the artificial respiration device 1 in the trachea 21. The hose 3 also protects the trachea 21 from the penetration of moisture, for example from the gullet 22.

What is claimed is:

1. Artificial respiration device for giving artificial respiration to a human being or mammal, comprising a tube, having a proximal end and a distal end, the distal end to be passed through the mouth and the pharynx towards the end of the trachea, characterized in that the distal end of the tube (2) opens out in a flexible hose (3), wherein a proximal end of the hose (3) is fixed to the distal end of the tube, and a distal end of the hose (3) extending away from the tube (2), said hose (3) being made of a material or materials with certain memory, and in that the device comprises an insertion element (8) movably mounted inside the tube (2), said insertion element (8) having a proximal end and a distal end, the distal end of the insertion element (8) being detachably fixed to the distal end of the hose (3), and the proximal end of the insertion element (8) protruding from the proximal end of the tube (2), wherein the insertion element by means of the proximal end thereof is movable with respect to the tube (2) from a first position wherein the distal end of the insertion element (8) in essence exerts no pulling force on the distal end of the hose (3), to a second position, towards the distal end of the tube wherein the distal end of the insertion element (8) exerts a pulling force on the distal end of the hose (3) in order to make the hose (3) constrict.

2. Artificial respiration device according to claim 1, characterized in that the distal end of the hose (3) comprises openings (6), and the distal end of the insertion element (8) comprises hooks which can project through the openings (6) of the hose (3).

3. Artificial respiration device according to claims 1, characterized in that the distal end of the tube (2) is provided with flaps (7).

4. Artificial respiration device according to claims 1, characterized in that the hose (3) has a rectaculated base (4), covered with a thin flexible film (5).

5. Artificial respiration device according to claims 1, characterized in that the insertion element (8) is made of aluminium covered with a plastic.

* * * * *